US012494353B2

(12) United States Patent
Lee et al.

(10) Patent No.: US 12,494,353 B2
(45) Date of Patent: Dec. 9, 2025

(54) PLASMA GENERATION APPARATUS

(71) Applicant: FEAGLE CO., LTD, Yangsan-si (KR)

(72) Inventors: Hyunyoung Lee, Yangsan-si (KR); Eunji An, Yangsan-si (KR); Jaesik Kim, Bucheon-si (KR); Intae Kim, Yangsan-si (KR); Jeonghae Choi, Busan (KR)

(73) Assignee: FEAGLE CO., LTD, Yangsan-si (KR)

( * ) Notice: Subject to any disclaimer, the term of this patent is extended or adjusted under 35 U.S.C. 154(b) by 251 days.

(21) Appl. No.: 18/270,838

(22) PCT Filed: Dec. 30, 2021

(86) PCT No.: PCT/KR2021/020248
§ 371 (c)(1),
(2) Date: Jul. 4, 2023

(87) PCT Pub. No.: WO2022/149795
PCT Pub. Date: Jul. 14, 2022

(65) Prior Publication Data
US 2024/0071735 A1 Feb. 29, 2024

(30) Foreign Application Priority Data
Jan. 5, 2021 (KR) ........................ 10-2021-0001110

(51) Int. Cl.
*H01J 37/32* (2006.01)
*A61N 1/44* (2006.01)

(52) U.S. Cl.
CPC .......... *H01J 37/32844* (2013.01); *A61N 1/44* (2013.01)

(58) Field of Classification Search
None
See application file for complete search history.

(56) References Cited

U.S. PATENT DOCUMENTS 9,384,947 B2 * 7/2016 Watson ................. A61M 15/02
10,143,510 B2 * 12/2018 Nettesheim .............. H05H 1/24
(Continued)

FOREIGN PATENT DOCUMENTS

DE 102013113941 A1 * 6/2015 ........... A61B 18/042
KR 10-2016-0098216 A 8/2016
(Continued)

OTHER PUBLICATIONS

International Search Report in International Application No. PCT/KR2021/020248, dated Apr. 11, 2022 pages.

*Primary Examiner* — Srinivas Sathiraju
(74) *Attorney, Agent, or Firm* — Park, Kim & Suh, LLC

(57) ABSTRACT

Disclosed is a plasma generation apparatus which can efficiently generate plasma by using atmospheric air without separately supplying a gas for plasma generation, and is suitable for use in applications for skin care. A plasma generation apparatus according to an embodiment of the present invention comprises a plasma generation part including a plasma tip and configured to generate plasma within the plasma tip and deliver the plasma to an object. The plasma tip comprises: a tip body having an internal space in which the plasma is generated; an electrode part provided in the internal space within the tip body and configured such that power for generating the plasma is applied thereto; and an air inlet passage connecting an outer area of the tip body and the internal space so that air flows from the outer area of the tip body toward the electrode part.

9 Claims, 10 Drawing Sheets

(56) References Cited

U.S. PATENT DOCUMENTS

| | | | | |
|---|---|---|---|---|
| 10,266,802 | B2 * | 4/2019 | Ish-Yamini Tomer | C12M 35/08 |
| 10,827,598 | B2 * | 11/2020 | Vioel | H05H 1/2406 |
| 11,071,193 | B2 * | 7/2021 | Pichler | H10N 30/88 |
| 11,284,499 | B2 * | 3/2022 | Frame | H05H 1/2406 |
| 11,786,745 | B2 * | 10/2023 | Lee | H01J 37/3244 219/121.36 |
| 11,792,910 | B2 * | 10/2023 | Weilguni | H05H 1/2475 422/186.07 |
| 2015/0279629 | A1 * | 10/2015 | Liao | A61N 1/44 315/111.21 |
| 2016/0287310 | A1 * | 10/2016 | Nettesheim | H05H 1/24 |
| 2019/0046809 | A1 * | 2/2019 | Kang | H01J 37/32449 |
| 2019/0184187 | A1 * | 6/2019 | Lee | B01D 53/04 |
| 2020/0077503 | A1 * | 3/2020 | Pichler | H05H 1/2475 |
| 2020/0187342 | A1 * | 6/2020 | Vioel | H05H 1/2418 |
| 2020/0205277 | A1 * | 6/2020 | Kim | H01J 37/32449 |
| 2021/0360768 | A1 * | 11/2021 | Zeper | A61N 1/0464 |
| 2023/0084380 | A1 * | 3/2023 | Lee | H01J 37/3244 315/111.21 |
| 2023/0285630 | A1 * | 9/2023 | Short | A61L 26/008 |
| 2023/0414811 | A1 * | 12/2023 | Lawless | A61L 9/20 |
| 2024/0071735 | A1 * | 2/2024 | Lee | H01J 37/32844 |
| 2024/0419075 | A1 * | 12/2024 | Lee | G03F 7/16 |

FOREIGN PATENT DOCUMENTS

| | | | | |
|---|---|---|---|---|
| KR | 20160098216 | A * | 8/2016 | A61B 18/042 |
| KR | 10-2017-0022839 | A | 3/2017 | |
| KR | 10-2019-0041874 | A | 4/2019 | |
| KR | 10-1973020 | B1 | 4/2019 | |
| KR | 10-1978057 | B1 | 5/2019 | |
| KR | 10-2018180 | B1 | 9/2019 | |
| KR | 10-2020-0117466 | A | 10/2020 | |

* cited by examiner

PLASMA GENERATION APPARATUS

CROSS-REFERENCE TO RELATED APPLICATIONS

This application is a National Phase Application of PCT International Application No. PCT/KR2021/020248, which was filed on Dec. 30, 2021, and which claims priority from Korean Patent Application No. 10-2021-0001110 filed on Jan. 5, 2021. The disclosures of the above patent applications are incorporated herein by reference in their entirety.

TECHNICAL FIELD

The present invention relates to a plasma generation apparatus, and more particularly, to a plasma generation apparatus that may efficiently generate plasma using atmospheric air without supplying a separate gas for generating the plasma, and particularly, is suitable for use for skin care.

BACKGROUND ART

The background art described below is not described as a widely known technology prior to the filing of the present invention but is intended to describe the background from which the present invention is derived. In general, the plasma generation apparatus generates plasma by exciting a gas for generating the plasma. To this end, the plasma generation apparatus includes an electrode to which power for generating the plasma is applied and a gas supply pipe for supplying a gas for generating the plasma toward the electrode. The plasma generation apparatus according to the related art may be advantageously used for purposes such as welding or treating a surface of a workpiece by emitting the plasma in a jet form but is not suitable for use in a beauty device for skin care, a medical device for treating a human body, or surface treatment of the medical device.

The plasma generation apparatus used for skin care needs to ensure that plasmarized gas is in sufficient contact with a skin to enhance a skin care effect and should also prevent the skin from being damaged by the plasma. Further, in the plasma generation apparatus, an ozone gas may be generated as a by-product during a plasma generation process. In particular, in the case of the plasma generation apparatus used for skin care, the ozone gas generated by the plasma needs to be efficiently removed so that the ozone gas has no harmful effect on the human body.

DETAILED DESCRIPTION OF THE INVENTION

Technical Problem

An aspect of the present invention provides a plasma generation apparatus that may efficiently generate plasma using atmospheric air without supplying a separate gas for generating the plasma and is suitable for use for skin care.

Further, another aspect of the present invention provides a plasma generation apparatus that may allow a plasmarized gas to be sufficiently in contact with a skin and may efficiently remove an ozone gas generated as a by-product in plasma.

Further, still another aspect of the present invention provides a plasma generation apparatus that may prevent a skin from being damaged by plasma and may easily replace a plasma generation unit and/or an ozone removal unit.

The technical problems to be achieved in the present invention are not limited to the technical problems mentioned above. The unmentioned still other technical problems may be clearly understood by those skilled in the art of the present invention from the following description.

Technical Solution

A plasma generation apparatus according to an embodiment of the present invention includes a plasma generation unit that includes a plasma tip and generates plasma in the plasma tip to transfer the generated plasma to an object.

The plasma tip may include a tip body having an internal space in which the plasma is generated, an electrode part which is provided in the internal space inside the tip body and to which power for generating the plasma is applied, and an air inlet passage communicating an outer area of the tip body and the internal space so that air is introduced from the outer area of the tip body toward to the electrode part.

The plasma generation apparatus according to the embodiment of the present invention may further include an electrode support part on which the electrode part is supported and in which an ozone suction passage through which an ozone gas incidentally generated in the plasma is suctioned is formed in a central portion thereof.

The tip body may include a nozzle part that is coupled to the electrode support part to surround the electrode part and transfers the plasma generated in the internal space to the object. The air inlet passage may be formed between the electrode support part and the nozzle part or formed to pass through the nozzle part.

The plasma generation apparatus according to the embodiment of the present invention may further include a boss part protruding from an inner diameter portion of the electrode support part to generate a vortex in the air introduced into the internal space through the air inlet passage.

The electrode part may include a dielectric, a first electrode coated on a first surface of the dielectric and a second electrode coated on a second surface of the dielectric. The dielectric may be formed in a ring shape having an open center to form the ozone suction passage.

The tip body may include a nozzle part that is coupled to the electrode support part, on which the electrode part is supported, to surround the electrode part and transfers the plasma generated in the internal space to the object. The nozzle part may have the ozone suction passage through which the ozone gas incidentally generated in the plasma is suctioned, and the air inlet passage may be formed to pass through the nozzle part.

The plasma generation apparatus according to the embodiment of the present invention may further include an ozone removal unit that removes the ozone gas suctioned through the ozone suction passage, and an ozone suction unit that suctions the ozone gas through the ozone suction passage by a suction fan or a vacuum pump and forms a negative pressure in the internal space.

The ozone removal unit may be disposed between the plasma generation unit and the ozone suction unit. The ozone removal unit may include a porous filter in which a plurality of holes are perforated in an ozone filter made of activated carbon or manganese dioxide.

The ozone removal unit may further include a first high efficiency particulate air (HEPA) filter that is provided between the plasma generation unit and the porous filter, suctions the ozone gas generated in the plasma generation unit, and removes impurities, and a second HEPA filter that is provided between the porous filter and the ozone suction unit and removes impurities generated in the porous filter.

The ozone removal unit further includes a vortex generation unit that is provided at an inlet of the porous filter, forms a vortex in the ozone gas introduced into the porous filter, and disperses the ozone gas into the porous filter. The vortex generation unit may include a porous sponge formed of an activated carbon material, a plastic shape structure, a fan structure that rotates by itself by suctioning the ozone gas, cotton, or a filter.

At least one of the plasma generation unit and the ozone removal unit may be provided as a replaceable module.

The plasma tip further may include a mesh network provided in the internal space and disposed between the electrode part and an end of the nozzle part to prevent the electrode part from being in direct contact with a skin.

Advantageous Effects of the Invention

According to an embodiment of the present invention, there is provided a plasma generation apparatus that may efficiently generate plasma using atmospheric air without supplying a separate gas for generating the plasma and is suitable for use for skin care.

Further, according to the embodiment of the present invention, there is provided a plasma generation apparatus that may allow a plasmarized gas to be sufficiently in contact with a skin and may efficiently remove an ozone gas generated as a by-product in plasma.

Further, according to the embodiment of the present invention, there is provided a plasma generation apparatus that may prevent a skin from being damaged by plasma and may easily replace a plasma generation unit and/or an ozone removal unit.

Meanwhile, effects that may be obtained in the present invention are not limited to the effects described above. The unmentioned other effects may be clearly understood by those skilled in the art to which the present invention pertains from the following description.

BEST MODE

Figure 1:
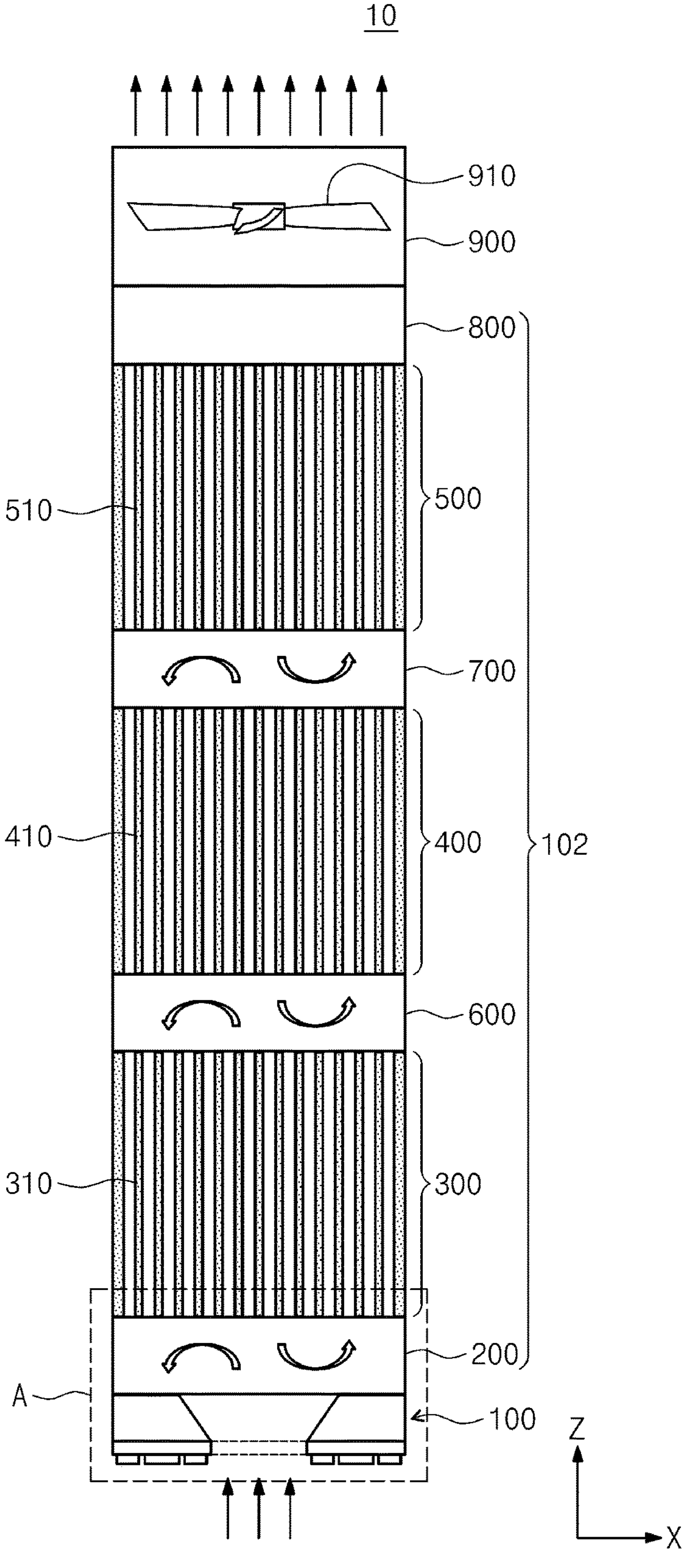
FIG. 1 is a schematic cross-sectional view illustrating a plasma generation apparatus according to an embodiment of the present invention.

Hereinafter, embodiments of the present invention will be described in more detail with reference to the accompanying drawings. The embodiments of the present invention may be modified into various forms, and the scope of the present invention should not be construed to be limited to the following embodiments. The embodiments of the present invention are provided to more completely describe the present invention for those skilled in the art.

It should be noted in advance that a configuration of the invention for clarifying the solution of the problem to be solved by the present invention will be described in detail with reference to the accompanying drawings based on an exemplary embodiment of the present invention, the same reference numerals are assigned to the same components even though the components are in different drawings in assigning reference numerals to components of the drawings, and components in other drawings may be cited when necessary in the description of the drawings.

A plasma generation apparatus according to an embodiment of the present invention may be particularly and suitably utilized for a portable skin care device or a personal skin care device but the embodiment of the present invention is not necessarily limited to this purpose.

The plasma generation apparatus according to the embodiment of the present invention includes a plasma generation unit that generates plasma in a plasma tip and transfer the plasma to an object. The plasma tip includes a tip body having an internal space in which the plasma is generated, an electrode part which is provided in the internal space of the tip body and to which power for generating the plasma is applied, and an air inlet passage through which an outer area of the tip body and the internal space of the tip body communicate with each other so that outside air is introduced from the outer area of the tip body toward the electrode part.

According to the embodiment of the present invention, the plasma may be efficiently generated using atmospheric air without supplying a separate gas to generate the plasma, and a separate gas supply pipe is not required so that the size and weight of the plasma generation apparatus may be reduced.

Further, in the plasma generation apparatus according to the embodiment of the present invention, a boss part may protrude from an inner diameter portion of an electrode support part in a columnar shape to generate a vortex in air introduced into the internal space of the tip body through the air inlet passage. Accordingly, an ozone gas is dispersed and uniformly absorbed into a porous filter, and at the same time, a stay time of the plasmarized gas increases so that the plasmarized gas is sufficiently in contact with a skin. Thus, the skin care effect may be improved.

Further, the plasma generation apparatus according to the embodiment of the present invention may include an ozone removal unit that is provided with an ozone suction passage through which the ozone gas generated in the internal space of the tip body may be suctioned and includes a porous filter having a plurality of perforated holes to remove the ozone gas suctioned through the ozone suction passage, and an ozone suction unit which forms a negative pressure in the internal space of the tip body and through which the ozone gas is suctioned.

The ozone removal unit may include a vortex generation unit that is provided at an inlet of the porous filter, forms a vortex in the ozone gas introduced into the porous filter, and disperses the ozone gas into the porous filter. Accordingly, the ozone gas is dispersed by the vortex generation unit and is uniformly suctioned into the porous filter, and at the same time, a time during which the ozone gas stays in the porous filter increases. Thus, the ozone gas generated as a by-product during a plasma generation process may be efficiently removed.

Further, in the plasma generation apparatus according to the embodiment of the present invention, at least one of the plasma generation unit and the ozone removal unit may be provided as a replaceable module. Accordingly, the plasma generation unit and/or the ozone removal unit that is a consumable component may be easily replaced. Further, the plasma generation apparatus according to the embodiment of the present invention may have a mesh network provided between the electrode part of the plasma tip and an end of a nozzle part, thereby preventing the skin from being damaged by the plasma.

Figure 2:
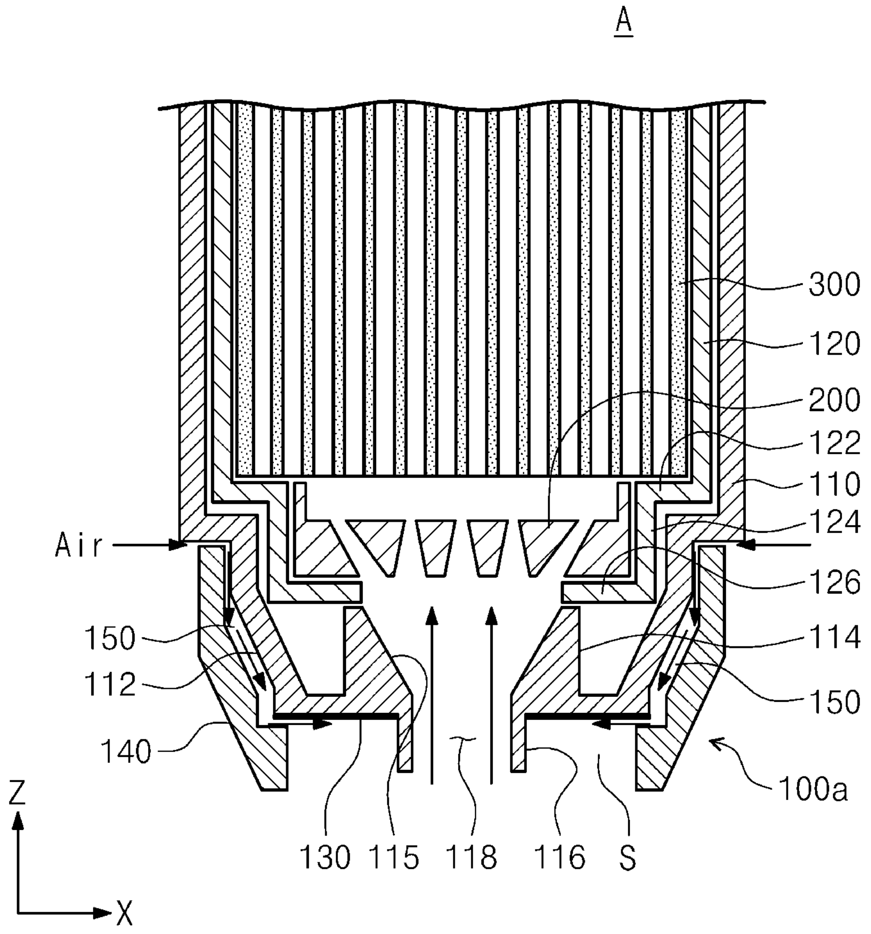
FIG. 2 is a cross-sectional view illustrating a portion of the plasma generation apparatus according to the embodiment of the present invention and is an enlarged view of part "A" of FIG. 1.
Figure 3:
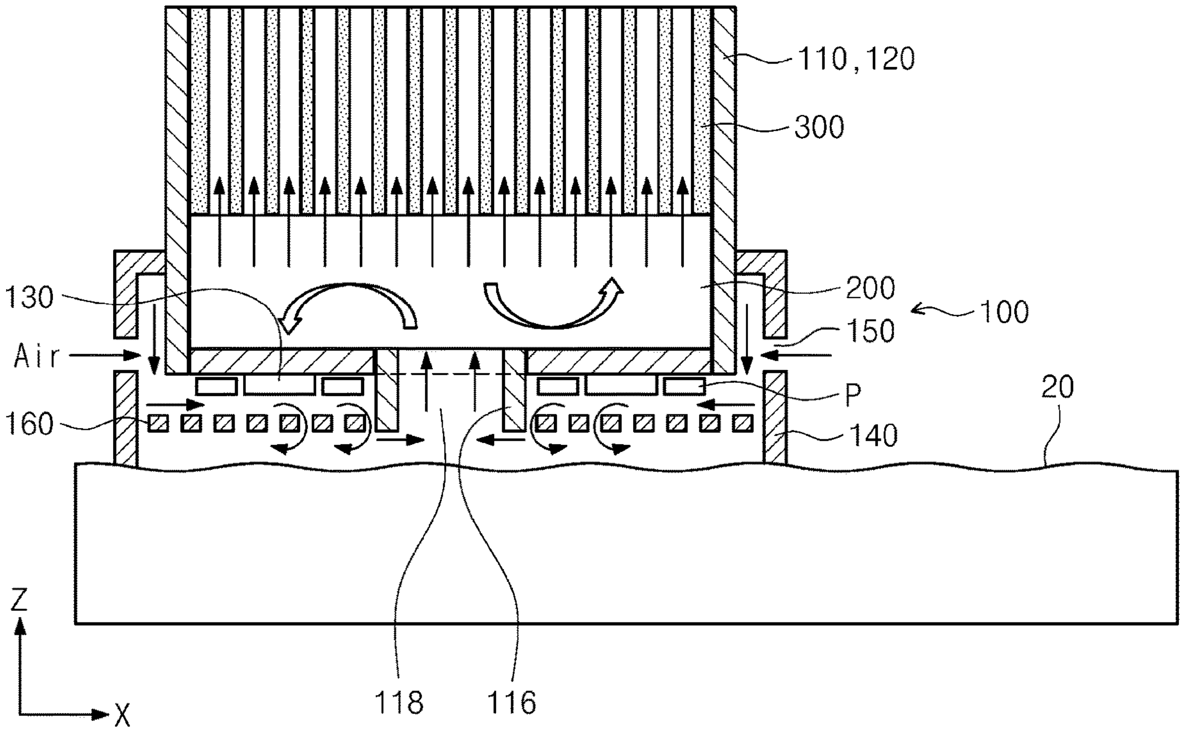
FIG. 3 is a conceptual diagram for describing an operation of a plasma tip constituting the plasma generation apparatus according to the embodiment of the present invention.

FIG. 1 is a schematic cross-sectional view illustrating a plasma generation apparatus according to an embodiment of the present invention. FIG. 2 is a cross-sectional view illustrating a portion of the plasma generation apparatus according to the embodiment of the present invention and is an enlarged view of part "A" of FIG. 1. FIG. 3 is a conceptual diagram for describing an operation of a plasma tip constituting the plasma generation apparatus according to the embodiment of the present invention.

Referring to FIGS. 1 to 3, a plasma generation apparatus 10 according to the embodiment of the present invention may include a plasma generation unit 100, an ozone removal unit 102, and an ozone suction unit 900.

The plasma generation unit 100 may include a plasma tip 100*a*. The plasma generation unit 100 may be configured to generate plasma inside the plasma tip 100*a* and transfer the generated plasma to an object (e.g., a human skin or the like).

The plasma tip 100*a* may include a tip body, for example, a nozzle part 140, having an internal space "S" in which the plasma is generated, an electrode part 130 provided in the internal space "S" inside the tip body, and an air inlet passage 150 for introducing outside air into the internal space "S".

The tip body of the plasma tip 100*a* may be made of an insulating material and may be made of, for example, a heat-resistant plastic or ceramic material having excellent thermal conductivity, excellent heat resistance, and excellent corrosion resistance to efficiently generate the plasma due to excellent insulation and high permittivity.

The tip body of the plasma tip 100*a* may be provided with the nozzle part 140 coupled to electrode support parts 110 and 120. The electrode support parts 110 and 120 may support the electrode part 130. The electrode support parts 110 and 120 may include the outer support part 110 and the inner support part 120.

The nozzle part 140 may be coupled to the electrode support parts 110 and 120 in various manners such as screwing, bolting, welding, and bonding to surround the electrode part 130. The nozzle part 140 may be configured to transfer the plasma generated in the internal space "S" in the tip body to the object (e.g., the human skin or the like).

The air inlet passage 150 may be formed between the outer support part 110 of the electrode support parts 110 and 120 and the nozzle part 140 or formed to pass through the nozzle part 140. The air inlet passage 150 may be formed to have a narrow gap so that a time during which the plasma stays in the internal space "S" may be ensured to a certain period of time.

The air inlet passage 150 may be formed in a tube shape having a small inner diameter or may be provided in a tubular shape coaxial with a central axis of the nozzle part 140. The air inlet passage 150 may extend from one side of the electrode support parts 110 and 120 or the nozzle part 140 to the internal space "S" in which the electrode part 130 is formed.

A tip member 112 of which a width decreases toward a plasma discharge part may be formed at a lower end of the outer support part 110. An ozone suction passage 118 through which the ozone gas incidentally generated in the plasma is suctioned may be formed at a center of the electrode support parts 110 and 120.

A support part 114 having an expansion surface 115 of which a width increases in a direction of suction flow of the ozone gas along the ozone suction passage 118 from the internal space "S" is formed in an inner diameter portion of the tip member 112.

The ozone gas generated as a by-product during a plasma generation process may be transferred to a first high efficiency particulate air (HEPA) filter 200 through the ozone suction passage 118. In this case, the ozone gas is spread along the support part 114 having the expansion surface 115 and is introduced into the first HEPA filter 200, and accordingly, a reaction area between the ozone gas and the first HEPA filter 200 may increase.

The inner support part 120 may be supported on the support part 114 of the outer support part 110. At a lower end of the inner support part 120, a first step 122 extending inward toward a central axis is formed and a vertical wall 124 extending downward from an inside of the first step 122 is formed. A second step 126 extending inward toward the central axis is formed at a lower end of the vertical wall 124.

The first HEPA filter 200 is supported by the vertical wall 124 and the second step 126. An inner diameter of the second step 124 may be designed to be the same as an inner diameter of an upper end of the support part 114.

Figure 4A:
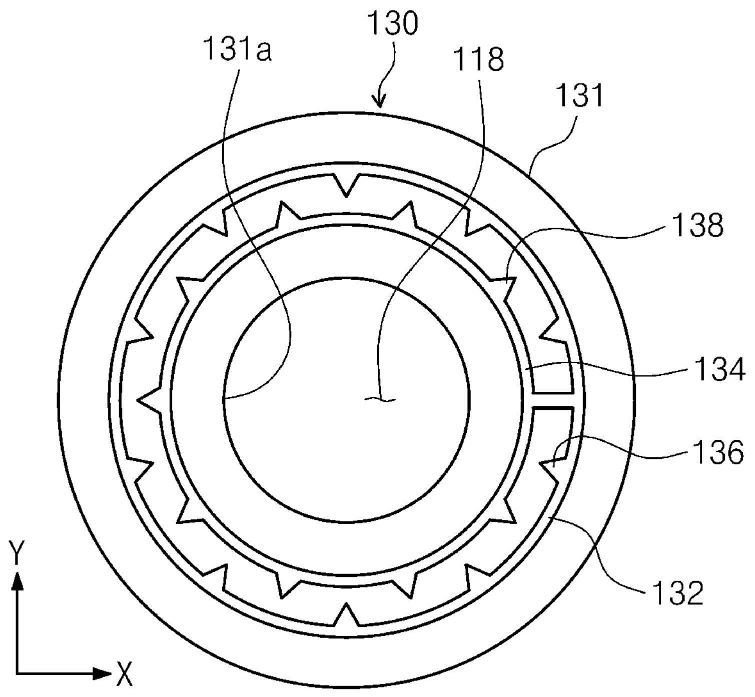
FIGS. 4A to 4C are bottom views illustrating an electrode part constituting a plasma generation apparatus according to various embodiments of the present invention.
Figure 4B:
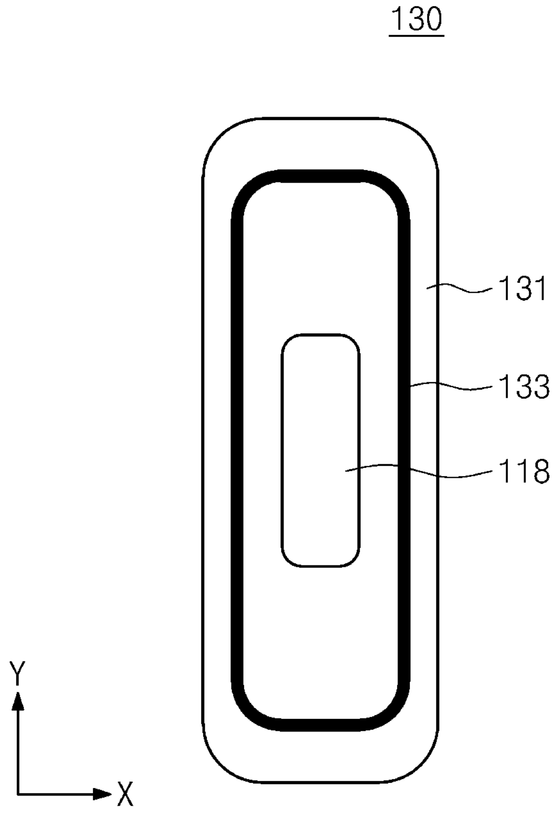
Figure 4C:
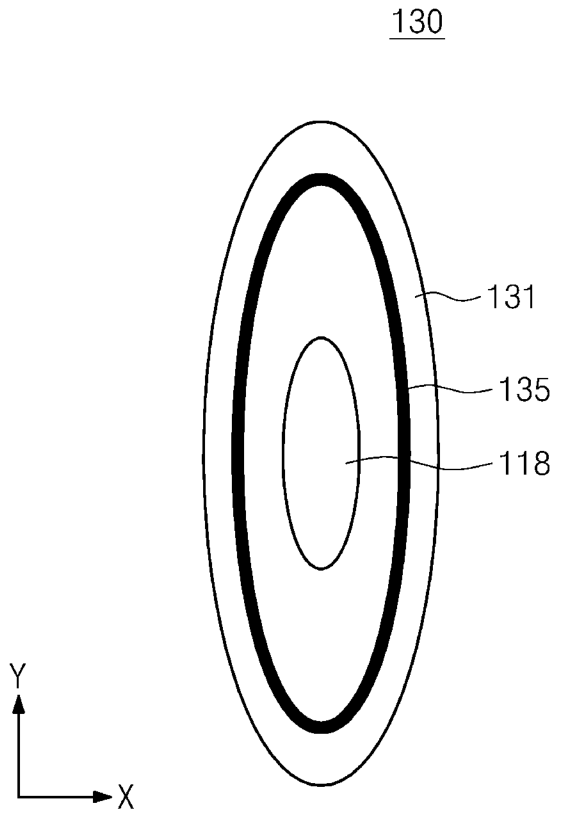

FIGS. 4A to 4C are bottom views illustrating an electrode part constituting a plasma generation apparatus according to various embodiments of the present invention. Referring to FIGS. 1 to 3 and FIGS. 4A to 4C, the electrode part 130 may be configured such that power for generating the plasma is applied thereto.

As described above, the outer area and the internal space "S" of the tip body may communicate with each other through the air inlet passage 150 so that air is introduced from the outer area of the tip body of the plasma tip 100*a* toward the electrode part 130.

The tip body may include a boss part 116. The boss part 116 may protrude from the inner diameter portion of the electrode support part 110 in a columnar shape to generate a vortex in the air introduced into the internal space "S" of the tip body through the air inlet passage 150.

In the gas plasmarized in the internal space "S" of the plasma tip 100*a*, the vortex occurs by the boss part 116 formed at a center of the plasma generation unit 100 and having the columnar shape. Accordingly, the gas that performs skin care or the like may be in sufficient contact with the human skin that is a plasma treatment target.

Further, the columnar structure of the boss part 116 may prevent the skin from being pressed or raised by pressure to directly come into contact with the plasma, thereby reducing the risk of electric shock due to a leakage current or the like and also serving to prevent a burn caused by heat generated in a plasma source.

The electrode part 130 may include a dielectric 131, first electrodes 132 and 134 coated on a first surface of the dielectric 131, and a second electrode (not illustrated) coated on a second surface of the dielectric 131. The dielectric 131 may be configured in a ring shape (a circular ring shape, a quadrangular ring shape having rounded corners, an oval ring shape, or the like) having an open central portion 131*a* to form the ozone suction passage.

The first electrodes 132 and 134 may include the outer electrode pattern 132 and the inner electrode pattern 134. The outer electrode pattern 132 and the inner electrode pattern 134 may be arranged concentrically and electrically connected to each other.

In the embodiment, the dielectric may be made of plastic materials such as ceramic (alumina), quartz, acetal, or polyether ether ketone (PEEK), but the present invention is not necessarily limited to these materials.

An electrode of the electrode part 130 may be formed of a conductive material such as metal. The electrode of the electrode part 130 may be made of, for example, nickel, copper, aluminum, tungsten, titanium, silver, or alloys of these materials, but the present invention is not limited thereto.

A dielectric coating or a metal coating such as tungsten coating or titanium coating, which may protect an electrode of a plasma generation surface that requires high durability, may be formed in the electrode. A metal pattern may be formed by a deposition process such as an e-beam and sputtering and may be printed in a silk screen method or the like.

The plasma generation surface (a surface facing the skin) of the electrode part 130 may be connected to the ground to prevent electrical shocks (e.g., leakage current and arc discharge flowing through the like), and a high voltage may be applied to a rear surface (a surface opposite to the skin).

To minimize an etching phenomenon by the plasma, a metal shape may be fired on a surface of the dielectric through a firing temperature of about 1000° C. or higher. The metal pattern may include protrusion patterns 136 and 138 to lower a discharge initiation voltage that is a plasma generation voltage.

The metal pattern of the electrode part 130 may be manufactured in various shapes such as a honeycomb structure or a ring shape, and a strength and amount of the plasma may be adjusted through the design of the shape of the metal pattern.

In the embodiment of FIG. 4A, the dielectric 131 and the first electrodes 132 and 134 have circular shapes. However, the electrode part 130 may include the dielectric 131 and an electrode 133 having quadrangular shapes having rounded corners as in the embodiment of FIG. 4B or may include the dielectric 131 and an electrode 135 having oval shapes as in the embodiment of FIG. 4C.

The ozone removal unit 102 may be configured to remove the ozone gas suctioned through the ozone suction passage 118. The ozone is a by-product generated from the plasma, is harmful to the human body, and thus should be necessarily removed.

The ozone suction unit 900 may be configured such that the ozone gas generated in the plasma generation unit 100 is suctioned through the ozone suction passage 118 by a suction fan 910 or a vacuum pump and a negative pressure is formed in the internal space "S" of the tip body.

Outside air is suctioned into a tip through a gap formed outside the plasma tip 100*a* by the negative pressure formed in the internal space "S" of the tip body, and the suctioned air may be ionized by the plasma generation unit 100 and thus converted into electrons, ions, charged particles, radicals, and the like.

Further, the ozone suction unit 900 may allow the ozone gas generated by the plasma generation unit 100 to pass through activated carbon filters or catalyst filters of porous filters 300, 400, and 500 so as to remove the ozone.

The ozone removal unit 102 may be disposed between the plasma generation unit 100 and the ozone suction unit 900. The ozone removal unit 102 may include the first HEPA filter 200, at least one porous filter 300, 400, and 500, at least one vortex generation unit 600 and 700, and a second HEPA filter 800.

The first HEPA filter 200 may be provided between the plasma generation unit 100 and the at least one porous filter 300, 400, and 500. The first HEPA filter 200 may suction the ozone gas generated by the plasma generation unit 100 to remove impurities.

The porous filters 300, 400, and 500 may be provided in structures in which a plurality of holes 310, 410, and 510 are perforated in ozone filters made of activated carbon (carbon-based) and/or manganese dioxide ($MnO2$) catalyst materials that are materials that may remove the ozone.

The activated carbon-based ozone filter has a limited lifetime because the filter directly reacts with the ozone to remove the ozone, but the manganese dioxide filter may be semi-permanently used because a catalytic reaction that does not directly react with itself occurs.

Using the porous filters 300, 400, and 500 having the structures in which the holes 310, 410, and 510 are densely perforated in the filters made of activated carbon or manganese dioxide, a surface area of the filter that reacts with the ozone and a speed at which the ozone gas passes therethrough may be appropriately controlled, and thus the ozone may be efficiently removed.

The porous filters 300, 400, and 500 may be manufactured in a honeycomb structure in which hexagonal holes are continuously perforated, a structure in which quadrangular holes are continuously perforated, or the like.

The surface area may be widened by the holes 310, 410, and 510 of the porous filters 300, 400, and 500, the speed at which the ozone gas passes therethrough may be reduced, and accordingly, an ozone removal efficiency may be increased.

Further, the perforated porous filters 300, 400, and 500 do not generate dust, have a relatively low density, and thus is light as compared to a circular columnar activated carbon and manganese dioxide catalyst according to the related art.

The vortex generation units 600 and 700 may be provided at inlets of the porous filters 400 and 500 and configured to form a vortex in the ozone gas introduced into the porous filters 400 and 500 to disperse the ozone gas to the porous filters 400 and 500.

The vortex generation units 600 and 700 may include a structure in which the vortex may be generated in the ozone gas, for example, a porous sponge made of a material such as activated carbon, a plastic structure, a fan structure that rotates by itself by suctioning the ozone gas, cotton having a certain thickness (e.g., cotton having a certain thickness and made of an activated carbon material), a filter, and the like.

The vortex generation units 600 and 700 may serve to generate the vortex so that the ozone suctioned by the plasma generation unit 100 may be uniformly dispersed into and pass through the porous holes of the porous filters 400 and 500. The ozone gas uniformly passes through the porous filters 400 and 500 by the vortex generation units 600 and 700, and accordingly, an ozone removal efficiency may increase.

The second HEPA filter 800 may be provided between at least one porous filter 300, 400, and 500 and the ozone suction unit 900. The second HEPA filter 800 may remove impurities generated from the porous filers 300, 400, and 500.

While the by-product generated in the plasma generation unit 100 primarily passes through the first HEPA filter 200, impurities having large particles are filtered out. Further, impurities that may be generated in the porous filters 300, 400, and 500 may be removed while passing through the second HEPA filter 800 mounted on an end.

A mesh network 160 may be provided in the internal space "S" of the tip body. The mesh network 160 may be disposed between the electrode part 130 and an end of the nozzle part 140 to prevent the electrode part 130 from being in direct contact with the skin.

Since the plasma generation apparatus according to the embodiment of the present invention generates the plasma using atmospheric air, there is no need to supply a separate gas (e.g., inert gas such as helium, neon, argon or nitrogen) for generating the plasma, and there is no need to provide a gas supply pipe for supplying the gas.

Accordingly, the plasma generation apparatus may be miniaturized and lightened, and particularly, may be suitably used as a portable personal skin care device. The plasma generation apparatus according to the embodiment of the present invention may be used for disinfection of a medical instrument, intraoral treatment, tooth whitening, tartar removal, implant fixture surface regeneration, scalp treatment, or skin treatment in addition to the skin care.

Figure 5:
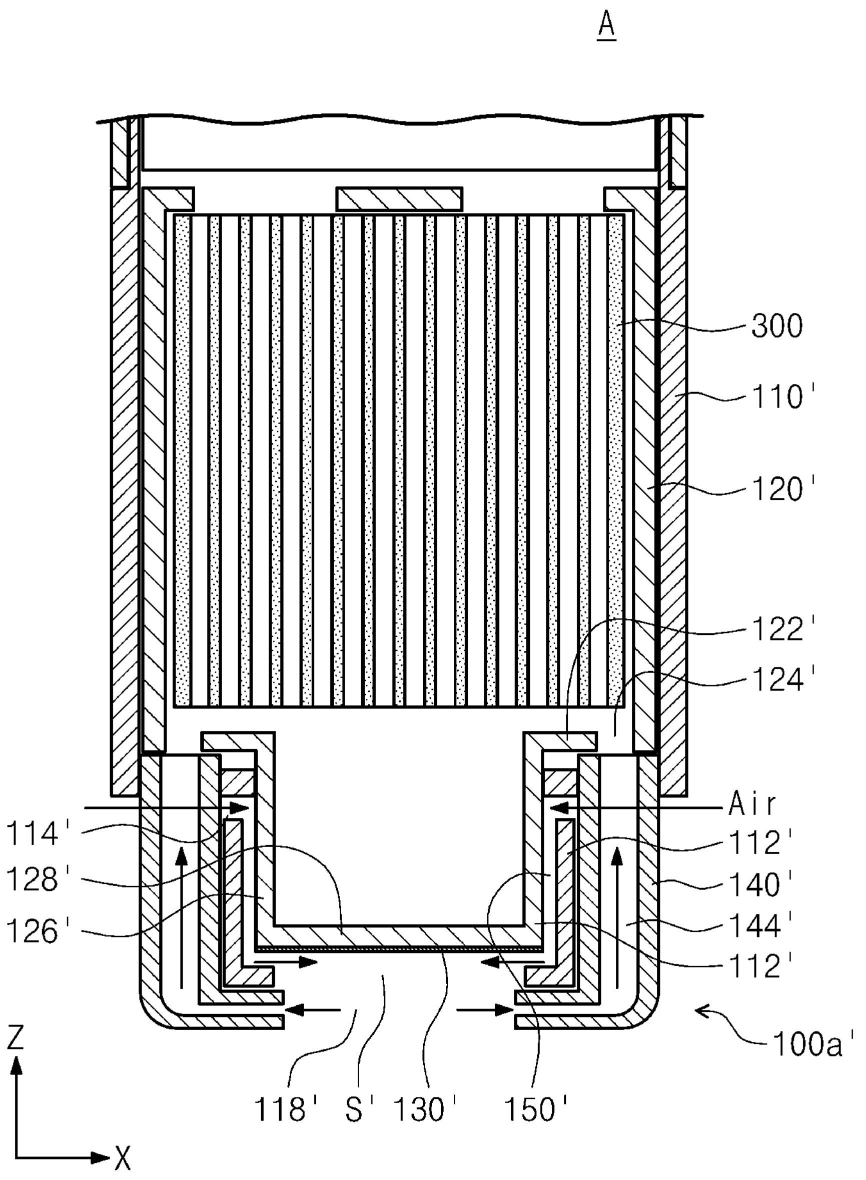
FIG. 5 is a cross-sectional view illustrating a portion of the plasma generation apparatus according to another embodiment of the present invention.
Figure 6:
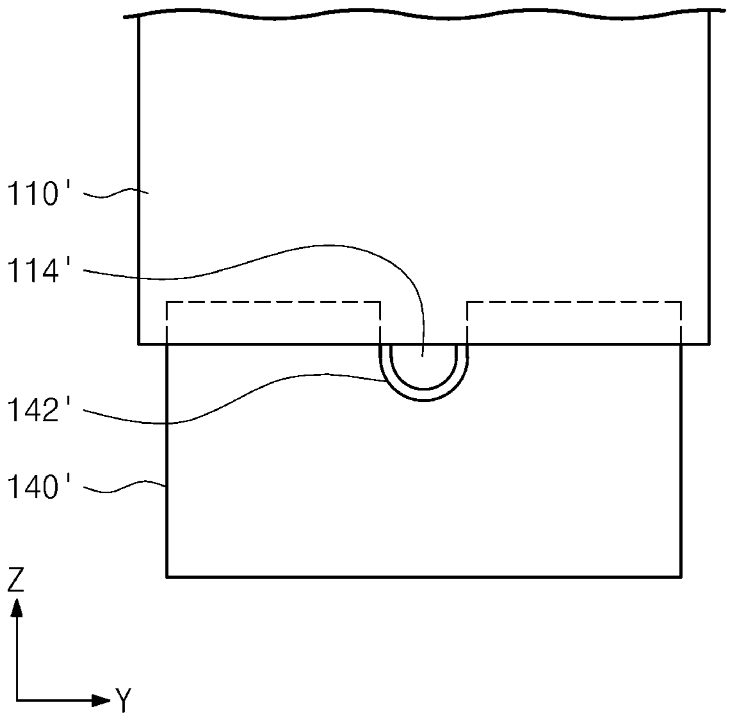
FIG. 6 is a side view illustrating a portion of the plasma generation apparatus illustrated in FIG. 5 according to the embodiment.

FIG. 5 is a cross-sectional view illustrating a portion of the plasma generation apparatus according to another embodiment of the present invention. FIG. 6 is a side view illustrating a portion of the plasma generation apparatus illustrated in FIG. 5 according to the embodiment.

Referring to FIGS. 5 and 6, a tip body of a plasma tip 100*a*' may include a nozzle part 140' coupled to electrode support parts 110' and 120', on which an electrode part 130' is supported, to surround the electrode part 130'. The nozzle part 140' may be configured to transfer the plasma generated in the internal space "S" of the tip body to the object.

The electrode support parts 110' and 120' may include the outer support part 110' and the inner support part 120'. The cylindrical nozzle part 140' may be coupled to a lower portion of the outer support part 110' through screwing, bolting, welding, bonding, or the like.

The inner support part 120' may be provided as a cylindrical part 126' having a bottom surface 128' that is blocked. An ozone suction hole 124' may be formed in a step part 122' of the inner support part 120'. The nozzle part 140' may include an ozone suction passage 144' through which the ozone gas incidentally generated in the plasma is suctioned. The ozone suction hole 124' may communicate with the ozone suction passage 144' formed in the nozzle part 140'.

An air inlet passage 114' may be formed through a side surface of the outer support part 110'. An air inlet passage 142' communicating with the air inlet passage 114' of the outer support part 110' may be formed on a side surface of the nozzle part 140'.

Further, an air inlet passage 150' communicating with the air inlet passage 114' of the outer support part 110' may be formed between the outer support part 110' and the inner support part 120' of the plasma tip 100*a*'.

In the plasma generation apparatus according to the embodiment of FIG. 5, outside air may be introduced into an internal space S', in which the electrode part 130' is positioned, through the air inlet passage 114' formed on the side surface of the outer support part 110', the air inlet passage 142' formed on the side surface of the nozzle part 140', and the air inlet passage 150' formed between the outer support part 110' and the inner support part 120'.

The outside air introduced into the internal space S' of the plasma generation apparatus is excited by power applied to the electrode part 130', and accordingly, the plasma may be generated from the outside air. The ozone gas generated as a by-product during the plasma generation process may be transferred to the porous filter 300 of the ozone removal unit through the ozone suction passage 144' formed in the nozzle part 140'. A vortex generation unit (not illustrated in FIG. 5) that generates a vortex in the ozone gas may be provided between an upper end of the ozone suction passage 144' and the porous filter 300.

Figure 7:
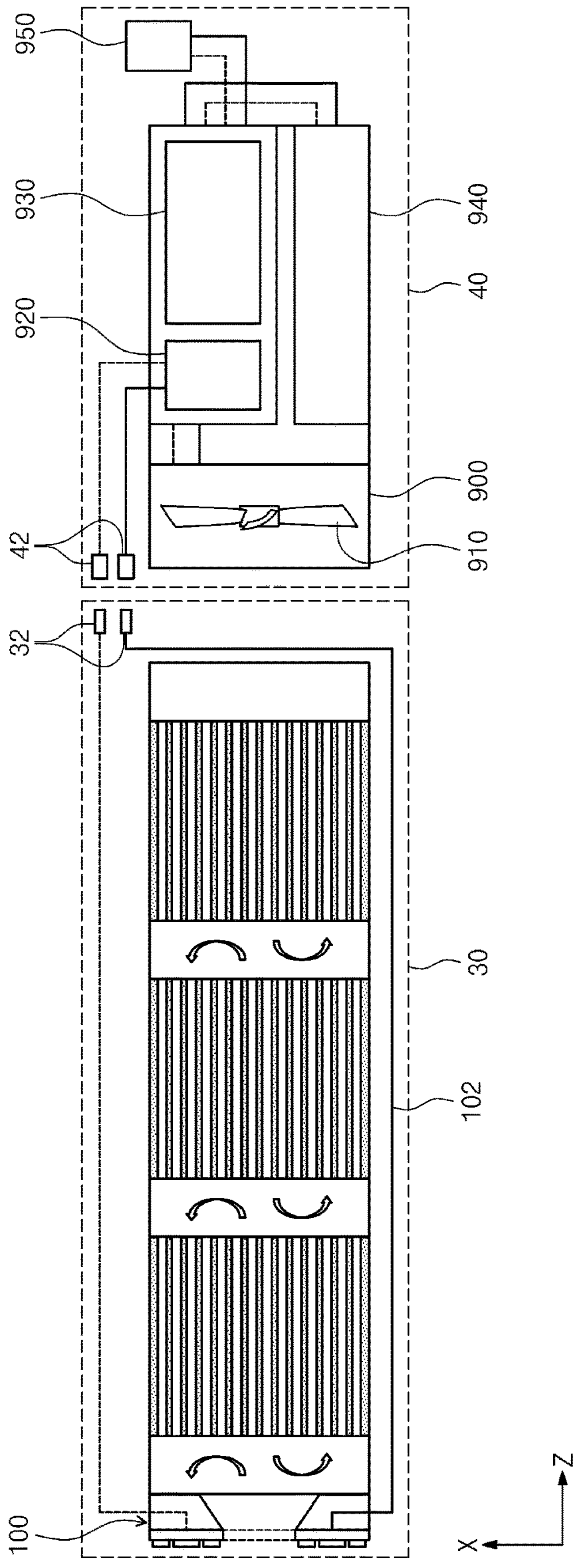
FIGS. 7 and 8 are schematic cross-sectional views illustrating a plasma generation apparatus according to still another embodiment of the present invention.
Figure 8:
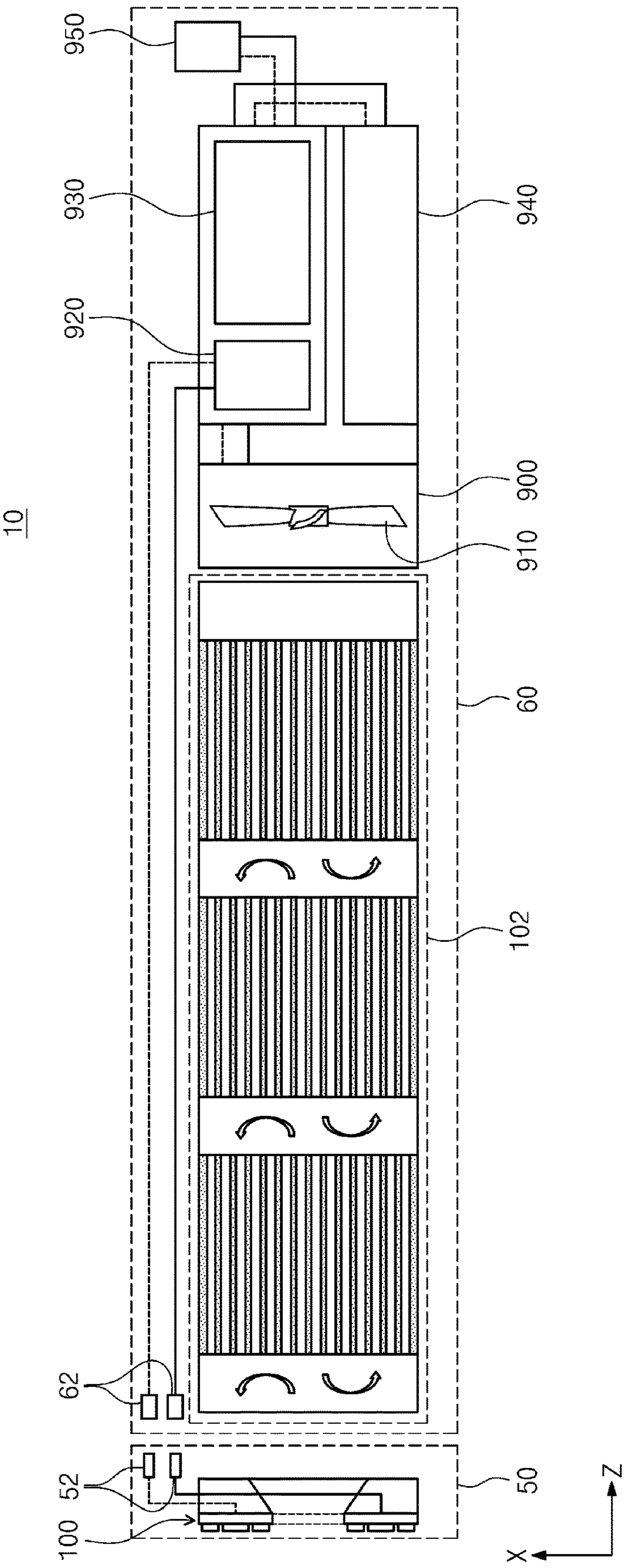

FIGS. 7 and 8 are schematic cross-sectional views illustrating a plasma generation apparatus according to still another embodiment of the present invention. Referring to FIGS. 7 and 8, at least one of the plasma generation unit 100 and the ozone removal unit 102 may be provided as a replaceable module so that the at least one of the plasma generation unit 100 and the ozone removal unit 102 is mechanically detachable.

The plasma generation unit 100 may be configured to receive an electrical signal using pogo pins 32, 42, 52, and 62, and accordingly, modules 30 and 50 including the plasma generation unit and/or the ozone removal unit that is a consumable component may be detached from bodies 40 and 60 and easily replaced.

The bodies 40 and 60 of a plasma generation device 10 may include a circuit part on which a high voltage circuit 920, a control circuit 930, a charging circuit 940, an ozone sensor 950, and the like are mounted and a battery part. The plasma generation unit 100 and/or the ozone removal unit 102 may be configured such that the corresponding modules 30 and 50 are detachably attached to the bodies 40 and 60. The plasma generation unit 100 and the ozone removal unit 102 may be made as one set and configured as a replaceable module together.

The above detailed description exemplifies the present invention. Furthermore, the above-mentioned contents describe the exemplary embodiment of the present invention, and the present invention may be used in various other combinations, changes, and environments. That is, the present invention may be modified and corrected without departing from the scope of the present invention that is disclosed in the specification, the equivalent scope to the written disclosures, and/or the technical or knowledge range of those skilled in the art.

The written embodiment describes the best state for implementing the technical spirit of the present invention, and various changes required in the detailed application fields and purposes of the present invention may be made. Accordingly, the detailed description of the present invention is not intended to restrict the present invention in the disclosed embodiment state. Furthermore, it should be construed that the attached claims include other embodiments.

The invention claimed is:

1. A plasma generation apparatus comprising:

a plasma generation unit including a plasma tip and configured to generate plasma in the plasma tip to transfer the generated plasma to an object, wherein the plasma tip includes:

a tip body having an internal space in which the plasma is generated;

an electrode part which is provided in the internal space inside the tip body and to which power for generating the plasma is applied; and an air inlet passage communicating an outer area of the tip body and the internal space so that air is introduced from the outer area of the tip body toward to the electrode part; and wherein the plasma generation apparatus further comprises an electrode support part on which the electrode part is supported and in which an ozone suction passage through which an ozone gas incidentally generated in the plasma is suctioned is formed in a central portion thereof, wherein the tip body includes a nozzle part coupled to the electrode support part to surround the electrode part and configured to transfer the plasma generated in the internal space to the object, wherein the air inlet passage is formed between the electrode support part and the nozzle part or formed to pass through the nozzle part, wherein the plasma generation apparatus further comprises:

an ozone removal unit configured to remove the ozone gas suctioned through the ozone suction passage; and an ozone suction unit configured to suction the ozone gas through the ozone suction passage by a suction fan or a vacuum pump and to form a negative pressure in the internal space, wherein the ozone removal unit is disposed between the plasma generation unit and the ozone suction unit, wherein the ozone removal unit includes a porous filter in which a plurality of holes are perforated in an ozone filter made of activated carbon or manganese dioxide.

2. The plasma generation apparatus of claim 1, further comprising:

a boss part protruding from an inner diameter portion of the electrode support part to generate a vortex in the air introduced into the internal space through the air inlet passage.

3. The plasma generation apparatus of claim 2, wherein the electrode part includes a dielectric, a first electrode coated on a first surface of the dielectric and a second electrode coated on a second surface of the dielectric, and the dielectric is formed in a ring shape having an open center to form the ozone suction passage.

4. The plasma generation apparatus of claim 1, wherein the tip body includes the nozzle part coupled to the electrode support part, on which the electrode part is supported, to surround the electrode part and configured to transfer the plasma generated in the internal space to the object, the nozzle part has the ozone suction passage through which the ozone gas incidentally generated in the plasma is suctioned, and the air inlet passage is formed to pass through the nozzle part.

5. The plasma generation apparatus of claim 1, wherein the ozone removal unit further includes:

a first high efficiency particulate air (HEPA) filter provided between the plasma generation unit and the porous filter and configured to suction the ozone gas generated in the plasma generation unit and remove impurities; and a second HEPA filter provided between the porous filter and the ozone suction unit and configured to remove impurities generated in the porous filter.

6. The plasma generation apparatus of claim 1, wherein the ozone removal unit further includes a vortex generation unit provided at an inlet of the porous filter and configured to form a vortex in the ozone gas introduced into the porous filter and disperse the ozone gas into the porous filter.

7. The plasma generation apparatus of claim 6, wherein the vortex generation unit includes a porous sponge formed of an activated carbon material or a fan structure that rotates by itself by suctioning the ozone gas.

8. The plasma generation apparatus of claim 6, wherein at least one of the plasma generation unit and the ozone removal unit is provided as a replaceable module.

9. The plasma generation apparatus of claim 1, wherein the plasma tip further includes a mesh network provided in the internal space and disposed between the electrode part and an end of the nozzle part to prevent the electrode part from being in direct contact with a skin.

* * * * *